United States Patent [19]
Crudden

[11] Patent Number: 5,985,798
[45] Date of Patent: Nov. 16, 1999

[54] N-ACYL SARCOSINATES AS GLYPHOSATE ADJUVANTS

[75] Inventor: Joseph J. Crudden, Hudson, N.H.

[73] Assignee: Hampshire Chemical Corp., Lexington, Mass.

[21] Appl. No.: 09/090,833

[22] Filed: Jun. 4, 1998

[51] Int. Cl.$^6$ .................................................. A01N 57/00
[52] U.S. Cl. ........................................................ 504/206
[58] Field of Search ...................................... 504/116, 206

[56] References Cited

U.S. PATENT DOCUMENTS

| | | | |
|---|---|---|---|
| 4,325,729 | 4/1982 | Rempfler et al. ............................ | 71/94 |
| 4,552,580 | 11/1985 | Aldwinckle ................................... | 71/3 |
| 5,543,383 | 8/1996 | Parker et al. ............................ | 504/116 |
| 5,686,391 | 11/1997 | Crudden ................................. | 504/258 |

OTHER PUBLICATIONS

Crudden et al., N–acyl sarcosinates: Effective, ecofriendly adjuvants for pesticide formulation, Book of Abstracts, 211th ACS National Meeting, New Orleans, LA, AGRO–194, American Chemical Society: Washington D.C., 1996.

Croda Chemicals Ltd. Crodasinic "N–acyl sarcosine derivatives Wetting and dispersing agents for pesticide formulations". 2–pages, no date available.

"The Properties and Potential Applications of a New Range of Chelating Surfactants"; J. Crudden, et al. pp. 1–14.

*Primary Examiner*—Jose' G. Dees
*Assistant Examiner*—Alton Pryor
*Attorney, Agent, or Firm*—Nields, Lemack & Dingman

[57] ABSTRACT

An adjuvant for glyphosate having increased activity, lower irritancy and lower toxicity than conventional adjuvants, and method of controlling weeds using the same. The adjuvant is $C_8$ to $C_{22}$ sarcosinate or sarcosinate salt, such as sodium cocoyl sarcosinate, sodium lauroyl sarcosinate, or combinations thereof, which is combined with glyphosate in low concentrations and provides effective activity.

15 Claims, No Drawings

N-ACYL SARCOSINATES AS GLYPHOSATE ADJUVANTS

BACKGROUND OF THE INVENTION

Glyphosate, or N-phosphonomethylglycine ($HOOCCH_2NHCH_2PO(OH)_2$), is a well-known translocated, postemergence, broadspectrum herbicide. The typical commercial formulation contains about 41% of the isopropylamine salt of glyphosate and is believed to contain about 16–20% by weight of a tallow amine ethoxylate surfactant. Glyphosate is a relatively insoluble acid, and thus is typically formulated and applied as a salt, such as the isopropylamine, sodium or ammonium salt.

Surfactants are incorporated into the formulation to improve the activity of the glyphosate. However, the term "surfactant" is ambiguous, as the form supplied by manufacturers is not necessarily a single compound, but can be a mixture. For example, with ethoxylated surfactants, the degree of ethoxylation can be and typically is a statistical mixture. The literature describes use of surfactants in glyphosate compositions and in particular, *Weed Science*, Vol. 25, pp 275–287 (1977) demonstrates the necessity of including a surfactant in glyphosate formulations. However, tallow amine ethoxylate is a severe eye irritant.

Conventional glyphosate formulations include the use of surfactants such as silicone to enhance the rainfast properties of glyphosate formulations. However, commercialization of such formulations has been hindered by the cost of incorporation of such surfactants into the formulations, and by the hydrolytic instability of such adjuvants. Other formulations including surfactants are disclosed in U.S. Pat. Nos. 5,362,705, 5,180,414 and 5,118,338.

Adjuvants are typically used in formulations to aid the operation or improve the effectiveness of the pesticide, herbicide, or other active ingredient. The term includes wetting agents, spreaders, emulsifiers, dispersing agents, foaming adjuvants, foam suppressants, penetrants, and correctives. For example, adjuvants such as Valent X-77® Spreader are commonly used to enhance the performance of Fluazifop-P-butyl, another selective herbicide. However, Valent X-77® Spreader and other ethoxylated nonionic surfactants contain free ethylene oxide which may form 1,4 dioxane, a known carcinogen.

It is therefore an object of the present invention to provide glyphosate adjuvants and formulations which do not suffer from the drawbacks of the prior art.

It is a further object of the present invention to provide herbicide formulations with excellent activity, lower irritancy and lower toxicity than conventional formulations.

It is yet another object of the present invention to provide efficacious glyphosate formulations with relatively low amounts of surfactant compared to conventional formulations.

SUMMARY OF THE INVENTION

The problems of the prior art have been overcome by the present invention, which provides an adjuvant for glyphosate having excellent activity, lower irritancy and lower toxicity than conventional adjuvants. The adjuvant is $C_8$ to $C_{22}$ sarcosinate or sarcosinate salt, such as sodium cocoyl sarcosinate, sodium lauroyl sarcosinate, the isopropylamine salt of oleoyl sarcosinate, the isopropylamine salt of cocoyl sarcosinate, or combinations thereof, which is combined with glyphosate and provides effective activity at equal or lower concentrations than conventional formulations.

DETAILED DESCRIPTION OF THE INVENTION

N-Acyl sarcosinates are mild biodegradable surfactants derived from fatty acid and sarcosine. Typically, sarcosinates are used in the form of their sodium, potassium, ammonium or isopropylamine salt solution. N-Acyl sarcosinates are produced commercially by the Schotten-Baumann reaction of the sodium salt of sarcosine with the appropriate fatty acid chloride under carefully controlled conditions:

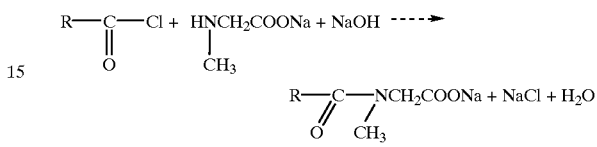

where R is typically a fatty acid of chain length $C_{10}$ to $C_{18}$, commonly made from lauric, coconut, palmitic, myristic or oleic acid. After the reaction is complete, the crude sodium salt is acidified to liberate the water insoluble free fatty sarcosinic acid which is separated from the aqueous by-products. It then is neutralized to a salt form with a suitable base, such as alkali metal hydroxide, ammonia, alkanolamines such as isopropanolamine, monoethanolamine or triethanolamine, or amino alcohols. Sarcosinates such as sodium lauroyl sarcosinate, sodium cocoyl sarcosinate and sodium myristoyl sarcosinate are commercially available under the trademark HAMPOSYL® from Hampshire Chemical Corp., as 30% active solutions in water.

The present inventor has found that $C_8$ to $C_{22}$ N-acyl sarcosinates, and in particular, the sodium and isopropylamine salts of cocoyl, oleoyl and lauroyl sarcosinate, are excellent adjuvants for glyphosate. The sarcosinates are low in phytotoxicity towards glyphosate tolerant crops, are low in toxicity, including aquatic toxicity, are low in irritancy (e.g., skin irritancy and ocular irritancy), and when combined with glyphosate at relatively low concentrations, cause the same to exhibit excellent activity. The formulations of the present invention exhibit extremely effective surface tension reduction to values below 25 dynes/cm, which should allow penetration through the stomata of the leaves, a highly efficient route of entry unavailable to systems containing tallow amine ethoxylate which cannot depress surface tension below 30 dynes/cm.

Suitable salts of these sarcosinates that are useful in the present invention include monoethylamine; diethylamine; triethylamine; alkali metal salts, particularly sodium and potassium; isopropylamine; and ammonia or amino alcohols such as tris amino or 2-dimethylamino-2-methyl-1-propanol.

Preferably the 30% sarcosinate solutions are used so that the final concentration of sarcosinate in the formulation is from about 2 to about 16% in the typical commercial formulation of 41% glyphosate isopropylamine salt. Higher sarcosinate concentrations can be used, but concentrations within the aforementioned range are preferred in view of the lower overall cost involved and in view of the desire to minimize phytotoxicity. For these reasons, concentrations of 2–8%, most preferably 2–4%, are especially preferred.

The sarcosinates are compatible with a wide variety of cationic, nonionic and amphoteric surfactants, and these could be incorporated into the formulations to achieve various effects. Examples of suitable additional surfactants include quaternary ammonium compounds, sodium cocamphoprionate, sodium dodecyl sulfate, lauryl dimethyl amine oxide and lauryl pyridinium chloride. Sarcosinates are unexpectedly compatible with cationics over extended concentration ranges.

The sarcosinates are also compatible with a wide variety of pesticides, such as Fuzilade, Pursuit and glufosinate, and these can be incorporated into the formulations of the present invention to achieve multifunctional products. Similarly, compatible insecticide and fungicide actives also could be incorporated and could be especially useful in treating glyphosate tolerant crops.

A wide range of adjuvants, such as stickers, spreaders, humectants and rainfastness additives conventional in pesticide formulations also can be added.

The formulations can be prepared by first mixing the sarcosinate with water, and then mixing the glyphosate herbicide with the resulting surfactant solution. Since dry solid salts of both sarcosinate and glyphosate can be produced, dry solid formulations with sarcosinate as an adjuvant are within the scope of the present invention. Suitable salts useful for that purpose are alkali metal salts, especially the sodium salt, and alkanolamines.

Those skilled in the art will appreciate that the final concentration of glyphosate depends on the particular application. One common concentration is a 41% active glyphosate solution further diluted 80:1, although higher or lower effective concentrations of glyphosate can be used.

The invention is further illustrated by the following non-limiting examples.

EXAMPLE 1

Cocoyl sarcosine, 280 g, was carefully mixed with 59.11 g of isopropylamine. The resulting clear viscous liquid was dissolved in water to produce a clear solution with a pH of about 6.5.

Glyphosate acid, 169.07 g, was reacted with 90 g of isopropylamine in 122 g of distilled water in a closed vessel to produce a isopropylammonium glyphosate salt solution. (The closed vessel was necessary because the reaction is exothermic and isopropylamine boils at about 25° C.) The pressure within the vessel at first increases and then decreases as the reaction proceeds. The product, a clear viscous liquid, is miscible with water in all proportions and has a pH of about 6.5.

Isopropylammonium glyphosate, 20.49 g, 60% glyphosate IPA, was mixed with 0.6 g of the isopropylammonium cocoyl sarcosinate, and 29.7 g of distilled water was added to produce a 41% active glyphosate IPA solution equivalent in active concentration to commercial glyphosate formulations. The clear, low viscosity solution produced was easily pourable, had a pH of about 6.5, and was readily miscible with water in all proportions. The concentration of isopropylammonium cocoyl sarcosinate was 2%.

Solutions containing 4%, 8%, and 16% isopropylammonium cocoyl sarcosinate were produced in an analogous manner.

EXAMPLE 2

Oleoyl sarcosine, 349 g, was mixed with 59.11 g of isopropylamine. The resulting amber viscous liquid was soluble in water and produced a clear solution with a pH of about 6.5.

EXAMPLE 3

Lauroyl sarcosine, 270 g, was heated to just above its melting point and subsequently reacted with 59.11 g of isopropylamine. The resulting clear viscous liquid slowly solidified when allowed to cool to room temperature, but could easily be remelted. When dissolved in water, the product produced a clear solution with a pH of about 6.5.

EXAMPLE 4

Field evaluations for the 2%, 4%, 8% and 16% formulations prepared in Example 1 were carried out on four different weed species, namely, Cheatgrass (*Bromus Secalinus*), Henbit (*Lamium Amplexicaule*), Velvetleaf (*Abulilon Theophrasti*) and Palmer Ameranth (*Amerantus Palmeri*). Commercially available Roundup®, Roundup® Ultra, and isopropylammonium glyphosate without surfactant were used as controls. The formulations were tested at 0.25 lbs active ingredient per acre, half the recommended rate, in order to separate the various formulations on the basis of efficacy. The results are shown below in Tables 1–4:

TABLE 1

Plant Species: Cheatgrass (*Bromus Secalinus*)

| | | Percent Control | |
|---|---|---|---|
| SURFACTANT | Application Rate lbs. Active/acre | 7 Days After Treatment | 13 Days after Treatment |
| CIPA 2% | .25 | 60.0 | 95.7 |
| CIPA 4% | .25 | 40.0 | 91.0 |
| CIPA 8% | .25 | 43.3 | 94.7 |
| CIPA 16% | .25 | 49.3 | 91.3 |
| Roundup | .25 | 41.7 | 91.0 |
| Roundup Ultra | .25 | 44.0 | 92.0 |
| Glyphosate (No Adjuvant) | .25 | 45.0 | 88.3 |

TABLE 2

Plant Species: Henbit (*Lamium Amplexicaule*)

| CIPA 2% | .25 | 48.3 | 86.0 |
|---|---|---|---|
| CIPA 4% | .25 | 35.0 | 89.3 |
| CIPA 8% | .25 | 38.3 | 80.3 |
| CIPA 16% | .25 | 46.7 | 78.3 |
| Roundup | .25 | 36.7 | 83.7 |
| Roundup Ultra | .25 | 43.3 | 84.0 |
| Glyphosate (No Adjuvant) | .25 | 35.0 | 73.3 |

TABLE 3

Plant Species: Velvetleaf (*Abulilon Theophrasti*)

| | | Percent Control | |
|---|---|---|---|
| SURFACTANT | Application Rate lbs. Active/acre | 7 Days After Treatment | 13 Days after Treatment |
| CIPA 2% | .25 | 48.3 | 95.7 |
| CIPA 4% | .25 | 33.3 | 93.3 |
| CIPA 8% | .25 | 56.7 | 96.7 |
| CIPA 16% | .25 | 60.0 | 90.7 |
| Roundup | .25 | 48.3 | 99.3 |
| Roundup Ultra | .25 | 35.0 | 95.3 |
| Glyphosate (No Adjuvant) | .25 | 39.3 | 89.3 |

TABLE 4

Plant Species: Palmer Ameranth (*Amerantus Palmeri*)

| SURFACTANT | Application Rate lbs. Active/acre | Percent Control 7 Days After Treatment | 13 Days after Treatment |
|---|---|---|---|
| CIPA 2% | .25 | 86.7 | 98.7 |
| CIPA 4% | .25 | 83.0 | 98.7 |
| CIPA 8% | .25 | 82.3 | 99.3 |
| CIPA 16% | .25 | 86.7 | 96.7 |
| Roundup | .25 | 78.3 | 97.7 |
| Roundup Ultra | .25 | 91.0 | 97.3 |
| Glyphosate (No Adjuvant) | .25 | 80.7 | 94.0 |

The results demonstrate that the glyphosate formulation devoid of surfactant was the least effective. Glyphosate formulations with isopropylammonium cocoyl sarcosinate at concentrations of 2 and 4% were generally more effective than at concentrations of 8 and 16%. All of the isopropylammonium cocoyl sarcosinate formulations of the present invention were generally more effective than the Roundup® and Roundup® Ultra formulations.

EXAMPLE 5

The Bovine Corneal Opacity and Permeability Assay is an in vitro assessment of ocular irritation developed and published by Gautheron, P., Dukic, M., Alix, D., Sina, J. F., "Bovine Corneal Opacity and Permeability Test: An In Vitro Assay of Ocular Irritancy", *Fund. Appl. Toxicol.*, 18, 442–449 (1992). In accordance with the assay, bovine eyes are collected from an abattoir, and the corneas excised. Plastic cassettes, which mimic eye structure, are used as holders for test corneas. The posterior chamber is filled with cell support media to restore the natural shape of the cornea and to maintain cell viability. The anterior chamber is filled with the test agent, either liquid or solid, and incubated for 10 minutes or 4 hours, respectively. At the end of exposure, opacity is measured by passing visible light from an opacitometer through the cornea onto the surface of a light sensor. A clear cornea that is unchanged by the test material will allow the light to pass through and be detected by a light sensor. Opaque corneas will produce light scattering (Tyndall effect) and reduced detection proportional to the degree of ocular damage. After exposure, fluorescein is added to the anterior chamber of the cassette. The amount of dye which passes through the cornea to the posterior chamber indicates the degree of corneal permeability. An increase in permeability indicates corneal damage.

The bovine corneal cytotoxicity assay is used as an addition to the Bovine Corneal Opacity and Permeability Assay. In the former, 8 mm biopsies are removed from corneas after the Bovine Corneal Opacity and Permeability Assay is complete. The biopsied sections are incubated with 3-(4,5-dimethylthiazol-2-yl)-2,5-diphenyltetrazolium bromide (MTT) to determine whether the degree of corneal viability remaining after exposure to test materials.

MTT dye, the indicator of cell viability used in this assay, is incorporated into living cells via the mitochondria. This results in the formation of insoluble purple formazin crystals which remain internal to the cells until extracted with isopropanol. The intensity of the extracted purple color in the alcohol is directly proportional to the viability of the tissues (i.e., the darker the purple color, the more cells are viable). Cell viability is inversely proportional to test agent toxicity; the less toxic a test product, the more cells are viable.

The results of the tests were as follows:

| SAMPLE | IN VITRO OPACITY @ 10 Min. | @ 30 Min. | MEAN % VIABILITY @ 30 Min. |
|---|---|---|---|
| Glyphosate IPA 41%, Oleoyl Sarcosinate IPA, 2% | 1.09 | 0.098 | 125 |
| Glyphosate IPA 41%, Oleoyl Sarcosinate IPA, 4% | 0.015 | 0.474 | 136 |
| Glyphosate IPA 41%, Cocoyl Sarcosinate IPA, 2% | 2.405 | 4.71 | 136 |
| Glyphosate IPA 41%, Cocoyl Sarcosinate IPA, 4% | 1.285 | 8.84 | 105 |
| Glyphosate IPA 41% | -0.9 | 3.247 | 110 |
| ROUNDUP ® | 1.030 | 2.339 | 44 |
| ROUNDUP ® ULTRA | 2.075 | 12.387 | 31 |
| Positive Control, BAC |  | 76.65 | 24 |
| Negative Control, Saline |  | 0 | N/A |

These results indicate that the formulations of the present invention are much less toxic to corneal tissue than the conventional formulations. The ROUNDUP® formulation yields a slightly lower opacity result than cocoyl sarcosine at 4% formulation, but a much higher tissue toxicity. The ROUNDUP® ULTRA formulation causes higher opacity and greater tissue toxicity than any of the formulations tested.

What is claimed is:

1. A herbicidal composition consisting essentially of a herbicidally effective amount of N-phosphonomethylglycine or a salt thereof, and an effective amount of an N-acyl sarcosinate adjuvant having the formula:

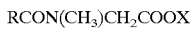

wherein R is $C_8$ to $C_{22}$ alkyl or alkenyl, and X is ammonium, $C_1$–$C_6$ alkylamine or an amino alcohol, said adjuvant being present in said composition in an amount greater than zero and up to about 8%.

2. The herbicidal composition of claim 1, wherein said N-phosphonomethylglycine is in the form of its isopropylamine salt.

3. The herbicidal composition of claim 1, wherein said N-acyl sarcosinate is selected from the group consisting of isopropylammonium salts of lauroyl sarcosinate, isopropylammonium salts of cocoyl sarcosinate, and a mixture of an isopropylammonium salt of lauroyl sarcosinate and an isopropylammonium salt of cocoyl sarcosinate.

4. The herbicidal composition of claim 2, wherein said N-acyl sarcosinate is selected from the group consisting of isopropylammonium salts of lauroyl sarcosinate, isopropylammonium salts of cocoyl sarcosinate, and a mixture of an isopropylammonium salt of lauroyl sarcosinate and an isopropylammonium salt of cocoyl sarcosinate.

5. The herbicidal composition of claim 1, wherein said adjuvant is isopropylammonium lauroyl sarcosinate.

6. The herbicidal composition of claim 1, wherein said adjuvant is isopropylammonium cocoyl sarcosinate.

7. The herbicidal composition of claim 1 in a dry solid form.

8. The herbicidal composition of claim 1, wherein said adjuvant is present in said composition in an amount greater than zero and up to 4%.

9. A method of controlling weeds in grass, comprising applying to said grass an effective amount of a herbicidal composition consisting essentially of N-phosphonomethylglycine or a salt thereof and an effective amount of an N-acyl sarcosinate adjuvant having the formula:

RCON(CH₃)CH₂COOX wherein R is $C_8$ to $C_{22}$ alkyl or alkenyl, and X is ammonium, $C_1$–$C_6$ alkylamine or amino alcohol, said adjuvant being present in said composition in an amount greater tan zero and up to about 8%.

10. The method of claim 9, wherein said N-phosphonomethylglycine is in the form of its isopropylamine salt.

11. The method of claim 9, wherein said adjuvant is isopropylammonium lauroyl sarcosinate.

12. The method of claim 9, wherein said adjuvant is isopropylammonium cocoyl sarcosinate.

13. The method of claim 9, wherein said adjuvant is present in said composition in an amount greater than zero and up to 4%.

14. A herbicidal composition consisting essentially of a herbicidally effective amount of N-phosphonomethylglycine or a salt thereof, an effective amount of an N-acyl sarcosinate adjuvant having the formula:

RCON(CH₃)CH₂COOX wherein R is $C_8$ to $C_{22}$ alkyl or alkenyl, and X is ammonium, $C_1$–$C_6$ alkylamine or an amino alcohol, said adjuvant being present in said composition in an amount greater than zero and up to about 8%, and a cationic, nonionic or amphoteric surfactant.

15. The herbicidal composition of claim 14, wherein said adjuvant is present in said composition in an amount greater than zero and up to 4%.

* * * * *